(12) United States Patent
Ha et al.

(10) Patent No.: US 11,510,772 B2
(45) Date of Patent: Nov. 29, 2022

(54) BIOMIMETIC ARTIFICIAL BLADDER

(71) Applicants: THE CATHOLIC UNIVERSITY OF KOREA INDUSTRY-ACADEMIC COOPERATION FOUNDATION, Seoul (KR); UNIVERSITY-INDUSTRY FOUNDATION, YONSEI UNIVERSITY, Seoul (KR); RESEARCH COOPERATION FOUNDATION OF YEUNGNAM UNIVERSITY, Gyeongsangbuk-do (KR)

(72) Inventors: U-Syn Ha, Seoul (KR); Jongbaeg Kim, Gyeonggi-do (KR); Won Gun Koh, Seoul (KR); Jin Ho Kim, Daegu (KR)

(73) Assignees: THE CATHOLIC UNIVERSITY OF KOREA INDUSTRY-ACADEMIC COOPERATION FOUNDATION, Seoul (KR); UNIVERSITY-INDUSTRY FOUNDATION, YONSEI UNIVERSITY, Seoul (KR); RESEARCH COOPERATION FOUNDATION OF YEUNGNAM UNIVERSITY, Gyeongsangbuk-do (KR)

( * ) Notice: Subject to any disclaimer, the term of this patent is extended or adjusted under 35 U.S.C. 154(b) by 193 days.

(21) Appl. No.: 16/481,262

(22) PCT Filed: Jan. 26, 2018

(86) PCT No.: PCT/KR2018/001154
§ 371 (c)(1),
(2) Date: Jul. 26, 2019

(87) PCT Pub. No.: WO2018/139890
PCT Pub. Date: Aug. 2, 2018

(65) Prior Publication Data

US 2019/0388212 A1 Dec. 26, 2019

(30) Foreign Application Priority Data

Jan. 26, 2017 (KR) .................. 10-2017-0012624

(51) Int. Cl.
*A61F 2/04* (2013.01)
*A61L 27/48* (2006.01)
*A61L 27/52* (2006.01)

(52) U.S. Cl.
CPC .............. *A61F 2/042* (2013.01); *A61L 27/48* (2013.01); *A61L 27/52* (2013.01);
(Continued)

(58) Field of Classification Search
CPC ................ A61F 2/042; A61F 2240/001; A61F 2250/0096; A61F 2/0036; A61F 2002/488;
(Continued)

(56) References Cited

U.S. PATENT DOCUMENTS 4,961,747 A 10/1990 Wascher et al.
2002/0193884 A1 12/2002 Wasserman et al.
(Continued)

FOREIGN PATENT DOCUMENTS

KR 10-2016-0103852 A 9/2016
KR 10-20160145015 A 12/2016
(Continued)

OTHER PUBLICATIONS

English translation of K20160103852A by Jo et al., Stretchable Strain Sensor and Sensing Methode of Vital Siganl by Using the Same, Dec. 19, 2016. (Year: 2016).*
(Continued)

*Primary Examiner* — Jerrah Edwards
*Assistant Examiner* — Rokhaya Diop

(74) *Attorney, Agent, or Firm* — Meunier Carlin & Curfman LLC

(57) ABSTRACT

Provided is an artificial bladder including: a main body which includes an inlet port, an outlet port, and a predetermined reservoir portion configured to store urine between the inlet port and the outlet port and is formed of a biocompatible polymer that is expandable so that a volume of the reservoir portion changes according to the amount of urine; a sensor which is attached to an outer wall of the main body, has a surface having a wrinkled structure, and is provided so that, when the volume of the reservoir portion increases, the wrinkled structure stretches out and resistance of the sensor changes; and an actuator which is provided at the outlet port and is configured to discharge the urine according a result detected by the sensor.

4 Claims, 4 Drawing Sheets

(52) U.S. Cl.
CPC . *A61F 2240/001* (2013.01); *A61F 2250/0096* (2013.01); *A61L 2400/12* (2013.01)

(58) Field of Classification Search
CPC ..... A61F 2250/0002; A61F 2210/0057; A61L 27/48; A61L 27/52; A61L 2400/12; A61L 27/26; A61L 27/50; A61L 2430/22; A61B 5/202; A61B 5/4851
See application file for complete search history.

(56) References Cited

U.S. PATENT DOCUMENTS

2013/0172664 A1    7/2013   Schmid et al.
2018/0243481 A1*   8/2018   Martin ..................... A61F 2/12

FOREIGN PATENT DOCUMENTS

| WO | 2015159185 A1 | 10/2015 |
| WO | 2016051333 A1 | 4/2016 |

OTHER PUBLICATIONS

International Search Report and Written Opinion. Issued by the International Searching Authority (ISA/KR) in application No. PCT/KR2018/001154 dated May 10, 2018. 11 pages, including English translation of International Search Report.

\* cited by examiner

[Figure 1]
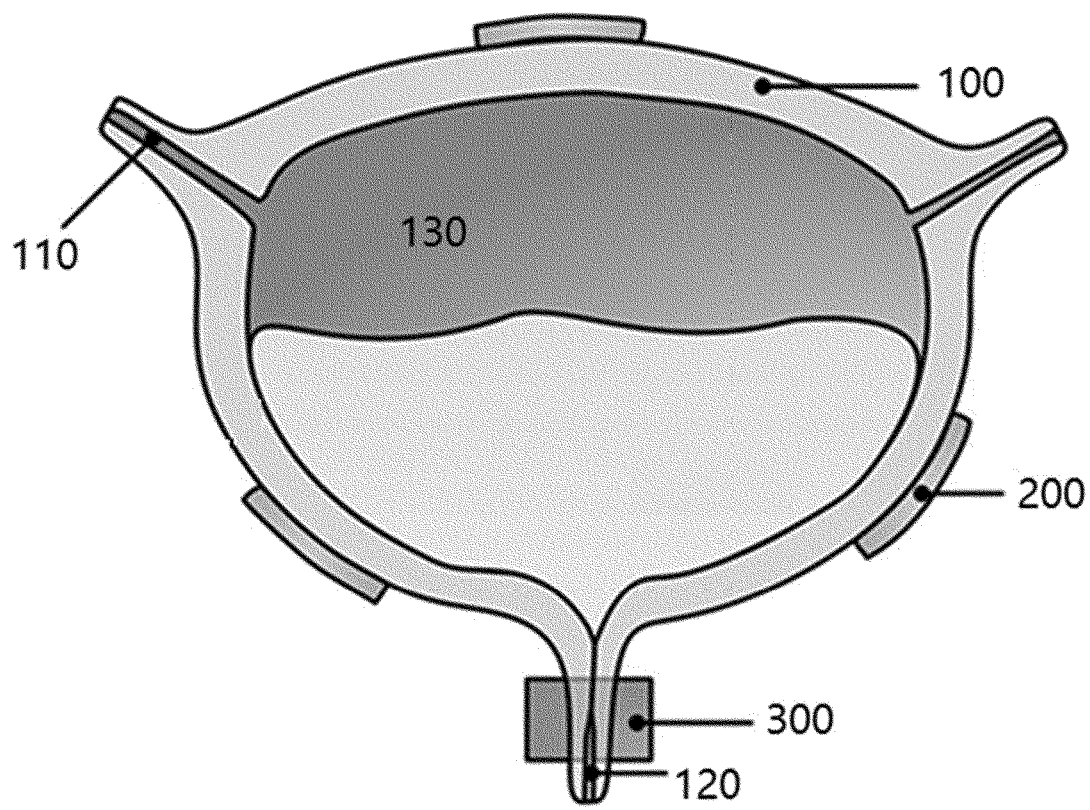
[Figure 2]
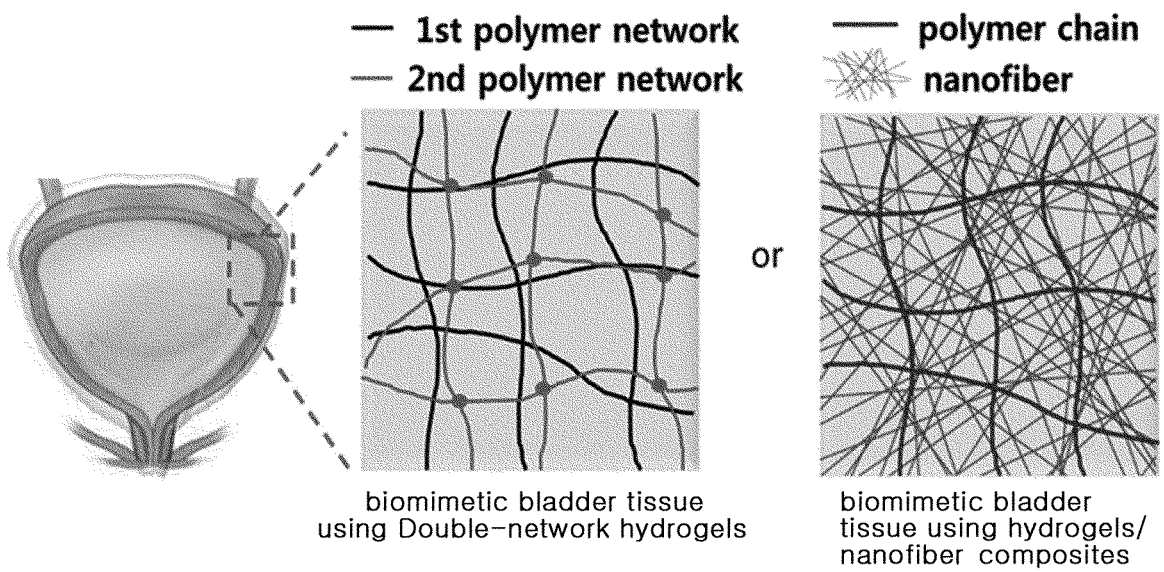

[Figure 3]
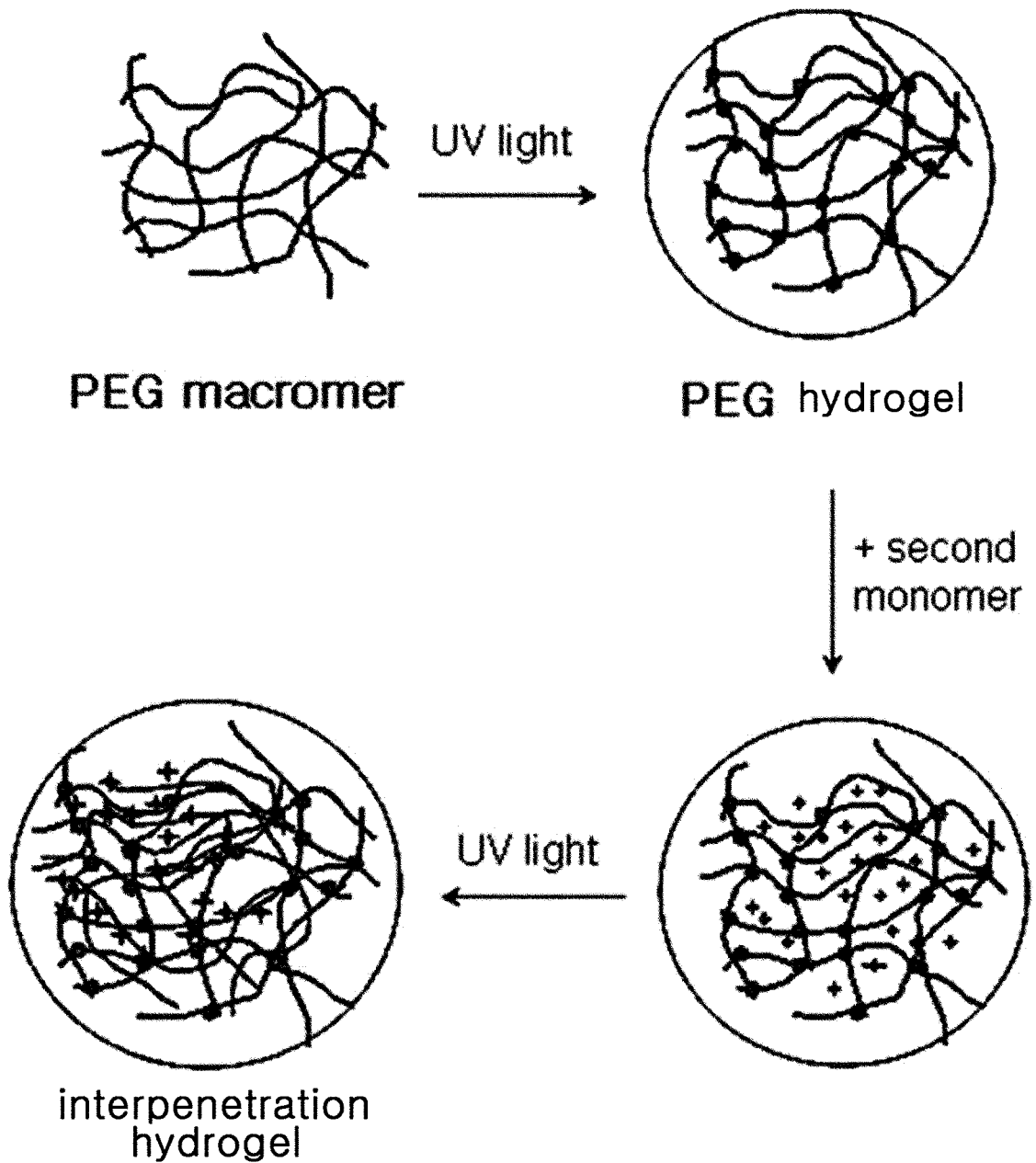

【Figure 4】
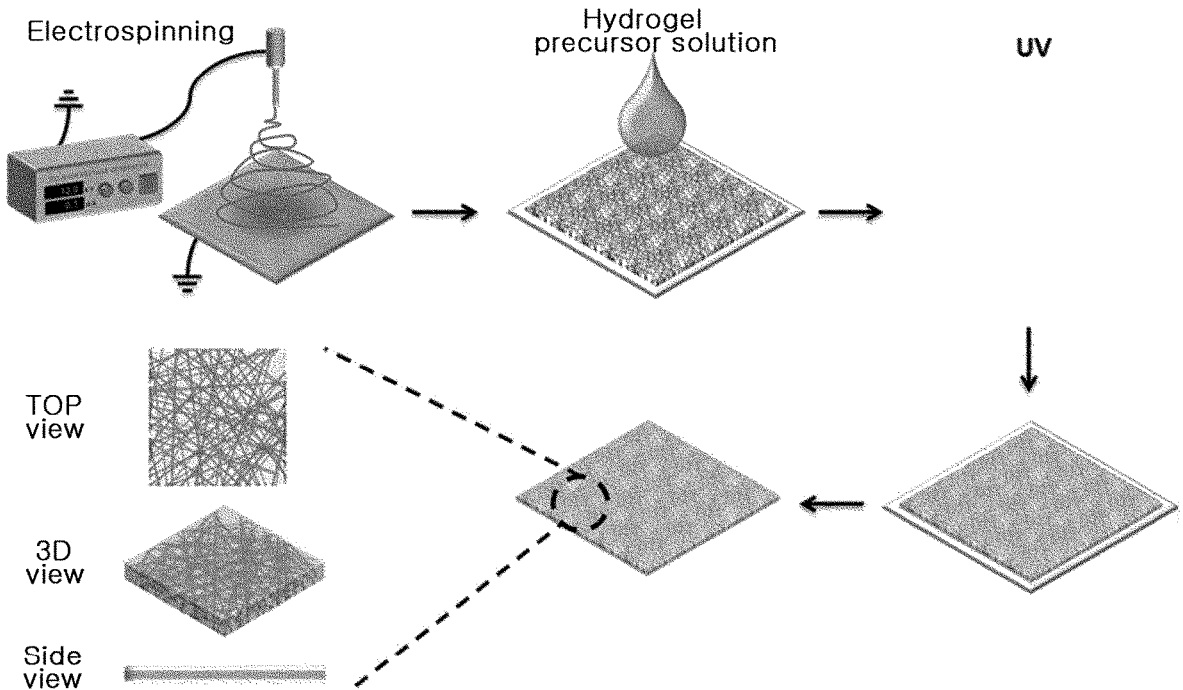
【Figure 5】
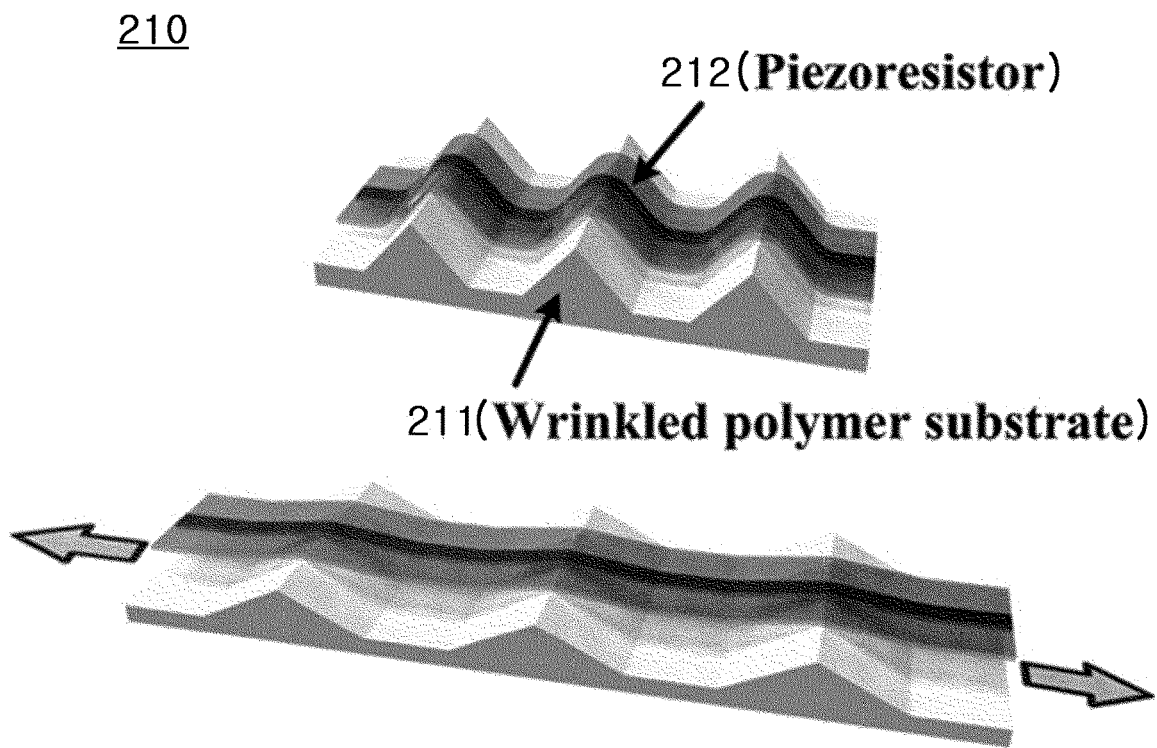

[Figure 6]
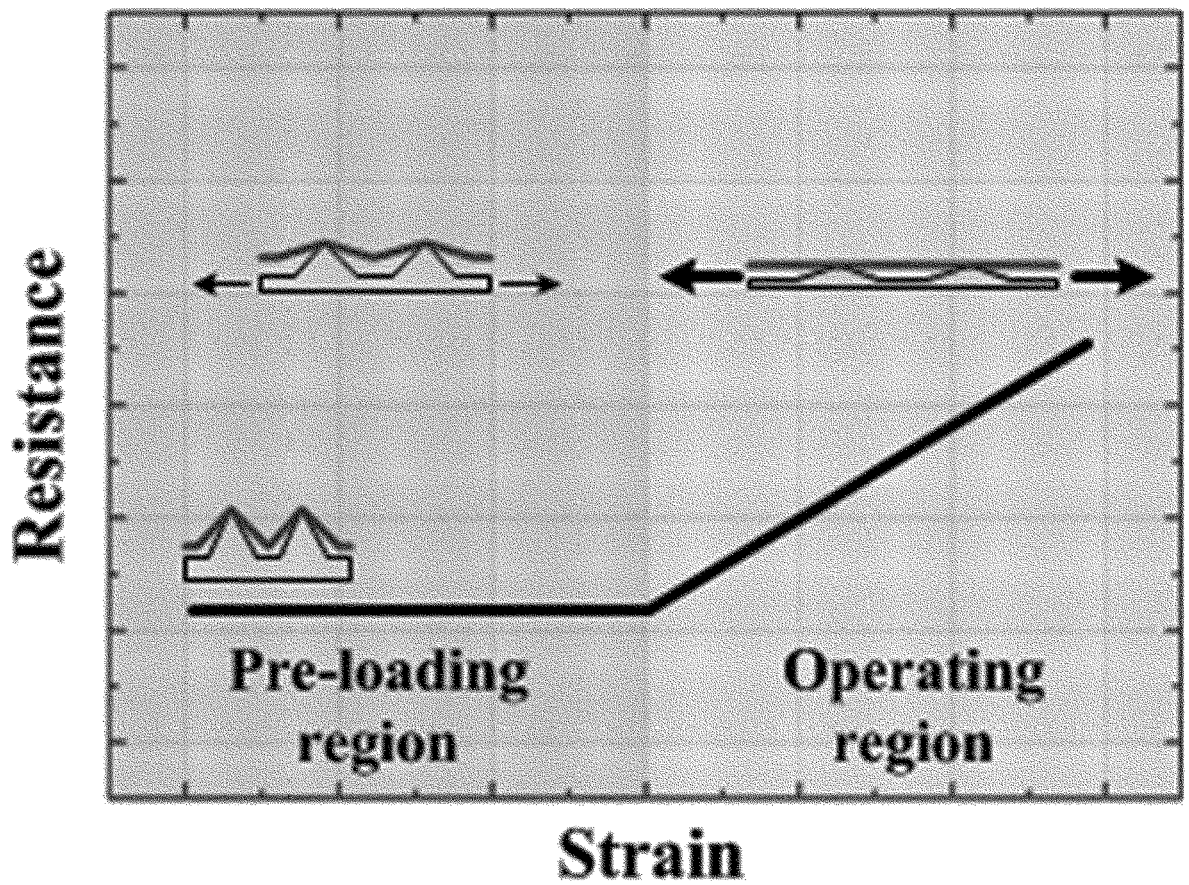
[Figure 7]
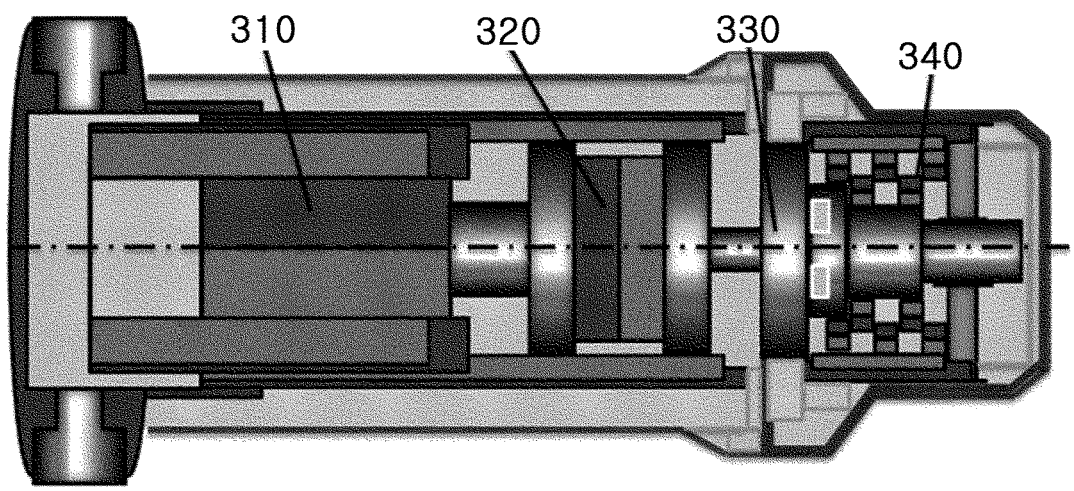

BIOMIMETIC ARTIFICIAL BLADDER

CROSS-REFERENCE TO RELATED APPLICATIONS

This application is a national stage application, filed under 35 U.S.C. § 371, of PCT/KR2018/001154, filed Jan. 26, 2018, which claims the benefit of and priority to Korean Patent Application No. 10-2017-0012624, filed Jan. 26, 2017, the disclosures of which are expressly incorporated herein by reference in their entirety.

TECHNICAL FIELD

The present invention relates to a biomimetic artificial bladder, and more particularly, to a biocompatible artificial bladder capable of replacing the human bladder.

BACKGROUND ART

Bladder cancer is the seventh most common cancer among males, the mortality rate of bladder cancer is the ninth highest among mortality rates of all cancers, and the number of bladder cancer patients is increasing by 10% or more every year in South Korea. Surgical treatment is absolutely necessary for the cure of bladder cancer, and cystectomy is performed on one-third of all bladder cancer patients.

Meanwhile, for a patient with nonfunctioning bladder due to spinal cord injury caused by external injury or due to neuromuscular failure caused by diabetic complications, due to irreversible changes in the muscles and nervous system of the bladder, there is no medication or surgical treatment capable of restoring the function of the bladder, and forced urination using a Foley catheter is the only urination method. Therefore, the patient must take out the ureter out of the body and wear a urinary drainage bag.

Existing methods of replacing an injured bladder include urinary diversion or forming a reservoir to store urine using a small intestine.

First, urinary diversion, i.e., a method in which the bladder is removed, the ureter is taken out of the body, and then urine is made to flow into a urinary drainage bag, may cause a change in an appearance of a patient and thus lead to a deterioration in the quality of life in terms of mental health.

Also, the case of forming a reservoir using a small intestine includes a method in which, by causing the small intestine of the patient to have a round shape and forming a reservoir, urine is stored in the body and indirectly induced to rise in the reservoir using an abdominal pressure so that the urine is discharged.

However, the small intestine is an organ that performs an absorbing function in terms of physiology, and thus, in the case in which an artificial bladder is formed using the small intestine, a problem may occur due to reabsorption of uremic toxins and electrolytes in urine upon urine storage. In addition, since the small intestine itself is unable to generate contractile force and thus there is no pressure rise in the reservoir, bladder fullness cannot be detected, effective urination is not performed, and thus there is a problem in that complications such as renal function deterioration or infection may occur.

Such limits of the existing bladder replacement techniques may, for bladder cancer patients, cause rejection or delay of bladder ablation and deteriorate treatment results and, for patients with nonfunctioning bladder, cause renal function deterioration and infection due to using a Foley catheter for a long period of time.

Therefore, there is a demand for development of an artificial bladder capable of overcoming such limits of the existing bladder replacement techniques.

DISCLOSURE

Technical Problem

The present invention provides a biocompatible artificial bladder capable of replacing the human bladder in order to overcome limits of existing bladder replacement techniques.

Technical Solution

One embodiment of the present invention provides an artificial bladder including: a main body which includes an inlet port, an outlet port, and a predetermined reservoir portion configured to store urine between the inlet port and the outlet port and is formed of a biocompatible polymer that is expandable so that a volume of the reservoir portion changes according to the amount of urine; a sensor which is attached to an outer wall of the main body, has a surface having a wrinkled structure, and is provided so that, when the volume of the reservoir portion increases, the wrinkled structure stretches out and resistance of the sensor changes; and an actuator which is provided at the outlet port and is configured to discharge the urine according a result detected by the sensor.

The biocompatible polymer may be formed of a hydrogel having a double-network structure.

The biocompatible polymer may be formed by cross-linking a hydrogel and a nanofiber.

The sensor may include a strain sensor configured to measure expansion and a shape change of the main body.

The strain sensor may be provided so that resistance thereof changes when strain of a predetermined value or more is applied.

The strain sensor may be formed of a piezoresistor which is formed of a nanomaterial film or a nanomaterial polymer composite and a polymer substrate which has a wrinkled structure.

The actuator may use a self-charging system using kinetic energy of the human body, without using an external battery.

Advantageous Effects

An exemplary artificial bladder of the present invention can provide, to patients who underwent cystectomy or patients with nonfunctioning bladder, an artificial bladder that is biocompatible and allows active urination.

DESCRIPTION OF DRAWINGS

FIG. 1 is a schematic diagram illustrating an artificial bladder according to the present invention.

FIGS. 2 to 4 are views illustrating a structure of a biocompatible polymer according to the present invention.

FIG. 5 is a schematic diagram illustrating a sensor according to the present invention.

FIG. 6 is a view for describing the sensor according to the present invention.

FIG. 7 is a schematic diagram illustrating an actuator according to the present invention.

MODES OF THE INVENTION

Hereinafter, exemplary embodiments of the present invention will be described in detail with reference to the accompanying drawings. Terms or words used in this specification and the claims are not to be interpreted as having general or dictionary meanings and should be interpreted as having meanings and concepts which correspond with the technical idea of the present invention based on the principle that the inventor can properly define the concept of the terms to describe his or her own invention in the best possible way.

Also, regardless of symbols in the drawings, elements which are identical or correspond to each other may be denoted by the same or similar reference numerals, and repetitive description thereof will be omitted. For convenience of description, the size and shape of each illustrated component may be exaggerated or reduced.

Therefore, embodiments described herein and configurations illustrated in the drawings are merely the most preferred embodiments of the present invention and do not represent the entire technical idea of the present invention, and thus, it should be understood that various equivalents and modifications, which can replace the most preferred embodiments, may be present at the time of filing this application.

The present invention relates to an artificial bladder. According to an exemplary artificial bladder according to the present invention, it is possible to provide an artificial bladder that is biocompatible and allows active urination.

FIG. 1 is a view schematically illustrating an exemplary artificial bladder according to the present invention.

As illustrated in FIG. 1, an artificial bladder 10 according to the present invention may be formed to include a main body 100, a sensor 200, and an actuator 300.

The main body 100 may include an inlet port 110, an outlet port 120, and a predetermined reservoir portion 130 configured to store urine between the inlet port and the outlet port.

The reservoir portion 130 may be formed of a biocompatible polymer that is expandable so that a volume of the reservoir portion 130 changes according to the amount of urine introduced via the inlet port 100.

More specifically, the inlet port 110 may perform a function of, for example, the human ureter, and the outlet port 120 may perform a function of, for example, the human urethra.

As illustrated in FIGS. 2 to 4, a biocompatible polymer may be used as a material of the artificial bladder 10, and the biocompatible polymer may be formed of a hydrogel having a double-network structure or may be formed by cross-linking a hydrogel and a nanofiber.

Here, referring to FIG. 3, regarding the hydrogel having a double-network structure, an interpenetration hydrogel, i.e., the hydrogel having a double-network structure, may be manufactured by, for example, exposing a polyethylene glycol (PEG) macromer to ultraviolet (UV) light to generate a PEG hydrogel and then irradiating the PEG hydrogel with UV light so that the PEG hydrogel forms a cross-link with a second monomer.

Also, referring to FIG. 4, for the polymer in which the hydrogel and the nanofiber form a cross-link, a hydrogel-nanofiber composite may be manufactured by spraying a hydrogel precursor solution on a nanofiber produced by electrospinning and then irradiating the nanofiber, on which the hydrogel precursor solution is sprayed, with UV light.

Here, for example, one or more natural or synthetic polymers selected from the group consisting of PEG, alginate, hyaluronic acid, poly lactic-co-glycolic acid (PLGA), and polycaprolactone (PCL) may be used as the biocompatible polymer, but the biocompatible polymer is not limited thereto.

Particularly, it is preferable to use natural or synthetic polymers usable in the human body that are approved by the U.S. Food and Drug Administration (FDA).

The main body formed of such biocompatible polymers has high compliance and high elasticity that allow the main body to accommodate itself to shape changes according to storage and discharge of urine.

Meanwhile, referring to FIG. 5, the sensor 200 may include a strain sensor 210 configured to measure expansion and a shape change of the main body 100. The strain sensor may be attached to an outer wall of the main body, formed of a piezoresistor 212 and a surface having a wrinkled structure 211, and provided so that, when the volume of the reservoir portion 130 increases, the wrinkled structure 211 stretches out and resistance of the sensor 200 changes.

More specifically, the strain sensor 210 may have a form in which the piezoresistor 212 is placed on a polymer substrate having the wrinkled structure 211.

Particularly, referring to FIG. 6, the strain sensor 210 may be provided so that, when strain of a predetermined value or more is applied, the resistance of the sensor 200 changes.

More specifically, the sensor may be manufactured to not operate in a pre-loading region, in which the amount of urine in the bladder is in a range of 0 ml to less than 100 ml, since the pre-loading region is irrelevant to whether urine is discharged and thus precise measurement of the amount of urine is not necessary therein, and may be manufactured to precisely measure the amount of urine in an operating region in which the amount of urine is in a range of 100 ml to 500 ml.

That is, in the pre-loading region, which is a region irrelevant to whether urine is discharged, the polymer substrate having the wrinkled structure 211 stretches out, but strain is not applied to the piezoresistor 212, while, in the operating region, strain begins to be applied to the piezoresistor 212 simultaneously as the polymer substrate having the wrinkled structure 211 stretches out such that the amount of urine may be measured from a change in resistance of the sensor 200 according to the applied strain, and a timing of urination may be determined.

Here, a nanomaterial film or a nanomaterial polymer composite may be used for the piezoresistor 212 of the strain sensor 210 so that the piezoresistor 212 has high sensitivity to sense even slight vibrations. For example, a carbon nanotube, graphene, a nanowire, and nanoparticles may be used for the nanomaterial film. The nanomaterial polymer composite may be any one or more selected from combinations of polymers such as polydimethylsiloxane (PDMS) and polyurethane (PU) and the above-mentioned nanomaterials. PDMS, PU, or the like may be used for the polymer substrate having the wrinkled structure 211.

Generally, the human bladder can store up to 500 ml of urine through volume expansion, and the bladder wall can stretch up to 70% or more. Therefore, the sensor applicable to the artificial bladder should also maintain the detecting function in a strain range of 70% or more in order to measure the amount of urine in the bladder.

The sensor 200 according to the present invention can stably measure the amount of urine in the bladder even under strain of 70% or more, on the basis of a flexible material of the wrinkled structure 211.

Meanwhile, the actuator 300 may be provided in the vicinity of the outlet port 120 of the main body 100 and driven to discharge the urine according to a result detected by the sensor.

The actuator 300 may include a motor 310, a linear actuator 320, an impeller 330, and an axial magnetic bearing 340.

The actuator 300 may be, for example, a pump. Particularly, the actuator 300 may be a linear pump but is not limited thereto.

More specifically, the sensor 200 and the actuator 300 may be interconnected with a controller 400 (not illustrated), and, through the controller, the amount of urine may be precisely monitored in real time, and urine may be controlled to be discharged according to active determination on a timing of urination.

For example, on the basis of a predetermined value for determining a timing of urination that is pre-input to the controller, when the sensor 200 detects that the amount of urine in the main body 100 is a predetermined value or more, the detected result is transmitted to the actuator 300 via the controller, and the actuator 300 operates so that the urine in the main body 100 is discharged via the outlet port 120.

For example, the predetermined value may indicate the amount of urine in the main body 100 and may be 250 ml or more or 300 ml or more but is not limited thereto.

The invention claimed is:

1. An artificial bladder comprising:
   a main body which includes an inlet port, an outlet port, and a predetermined reservoir portion configured to store urine between the inlet port and the outlet port and is formed of a biocompatible polymer that is expandable so that a volume of the reservoir portion changes according to an amount of urine in the reservoir portion;
   a strain sensor which is attached to an outer wall of the main body, is formed of a piezoresistor placed on a polymer substrate having a wrinkled structure, and is provided so that, when the volume of the reservoir portion increases, the wrinkled structure stretches out and a resistance of the strain sensor changes; and
   an actuator which is provided at the outlet port and is configured to discharge the urine according to a result detected by the strain sensor;
   wherein the strain sensor is configured to operate in a pre-loading region, in which the polymer substrate having the wrinkled structure stretches out but strain is not applied to the piezoresistor, and the strain sensor is configured to operate in an operating region, in which strain begins to be applied to the piezoresistor simultaneously as the polymer substrate stretches out, such that the amount of urine is measured from the change in the resistance of the strain sensor according to the applied strain, and a timing of urination is determined.

2. The artificial bladder of claim 1, wherein the biocompatible polymer is formed of a hydrogel having a double-network structure.

3. The artificial bladder of claim 1, wherein the biocompatible polymer is formed by cross-linking a hydrogel and a nanofiber.

4. The artificial bladder of claim 1, wherein the piezoresistor is formed of a nanomaterial film or a nanomaterial polymer composite.

* * * * *